United States Patent [19]

Czaban et al.

[11] 4,410,631
[45] Oct. 18, 1983

[54] COMPENSATED REFERENCE LIQUID

[75] Inventors: John D. Czaban, Bradford; Alan D. Cormier, Newburyport, both of Mass.

[73] Assignee: Instrumentation Laboratory Inc., Lexington, Mass.

[21] Appl. No.: 271,321

[22] Filed: Jun. 15, 1981

Related U.S. Application Data

[63] Continuation-in-part of Ser. No. 170,599, Jul. 21, 1980, abandoned.

[51] Int. Cl.³ .................. G01N 27/26; C09K 3/00
[52] U.S. Cl. ........................................ 436/8
[58] Field of Search ................... 252/408; 436/8

[56] References Cited

U.S. PATENT DOCUMENTS 3,556,950 1/1971 Dahms .................... 204/1
4,283,262 8/1981 Cormier .................. 73/53

FOREIGN PATENT DOCUMENTS 1156967 7/1969 United Kingdom .

OTHER PUBLICATIONS

Bates, Roger G. Pure Applied Chemistry, vol. 37(4), pp. 573–577, (1974).
Mohan, M. S. and Bates, Roger G., NBS Special Publication (U.S.), vol. 450, pp. 293–299, (1977).
Clinical Chemistry, vol. 25, No. 10, pp. 1865–1866, (1979).
Clinical Chemistry, vol. 26, No. 10, p. 1517, (1980).
Clinical Chemistry, vol. 26, No. 13, pp. 1921–1924.
Analytical Chemistry Symposium Series, vol. 2, pp. 45–46, (1980).
"Utility of Expressing Serum Sodium per Unit of Water in Assessing Hyponatremia", Waugh, William H., Metabolism, vol. 18, No. 8, (Aug. 1969), pp. 706–712.
"Liquid–Junction Potentials between Plasma or Erythrolysate and KCl Solutions," Salling, N., et al., Scand. J. Clin. Lab. Invest., vol. 28, No. 33, (1978), pp. 33–40.
"Normale Ranges for Serum Sodium by Ion–Selective Electrode Analysis Exceeds that by Flame Photometry," Annan, W., et al., Clin. Chem., vol. 25, No. 4, (1979), (Letters to the Editor).

Primary Examiner—Benjamin R. Padgett
Assistant Examiner—M. Moskowitz

[57] ABSTRACT

A reference liquid system for use with a chemical analyzer that has a plurality of ion selective electrodes comprises a plurality of reference liquids, each of which has a first salt component such that ions of a first element to be measured are present in a predetermined concentration, a second salt component such that ions of a second element to be measured are present in a predetermined concentration, and an error compensation salt component present in a concentration effective to adjust (a) the activity coefficient factor and/or
(b) the junction potential factor to reduce the error involved in use of the compensated reference liquid to less than fifty percent of the error involved in use of a corresponding uncompensated reference liquid.

24 Claims, 2 Drawing Figures

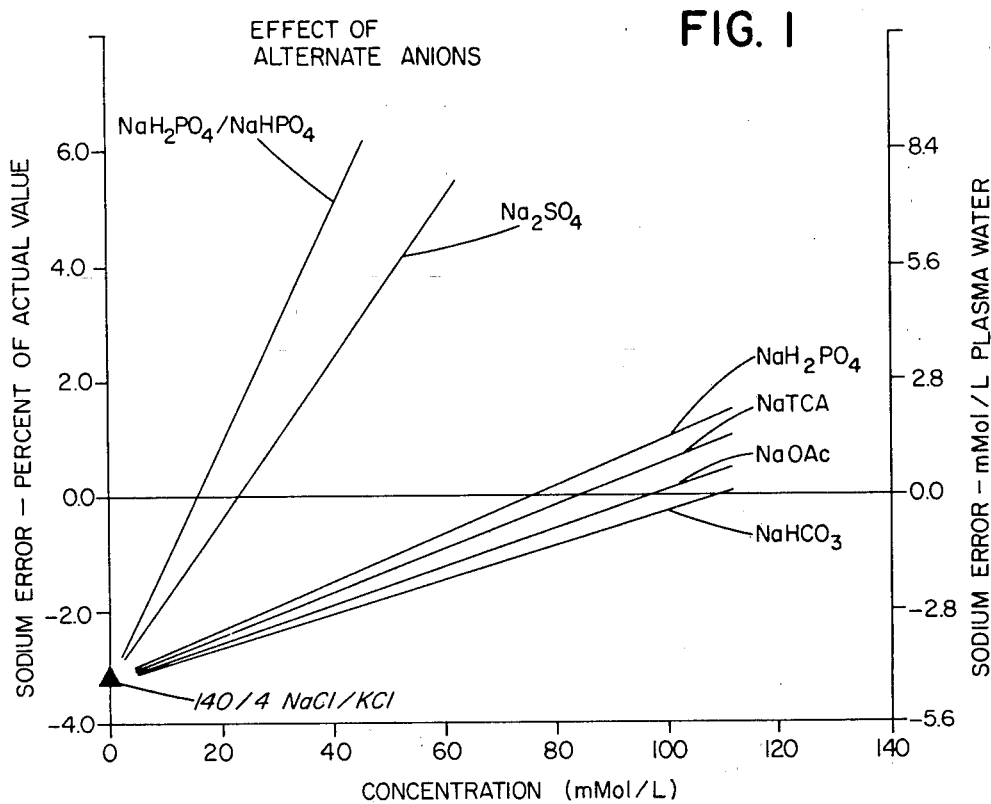
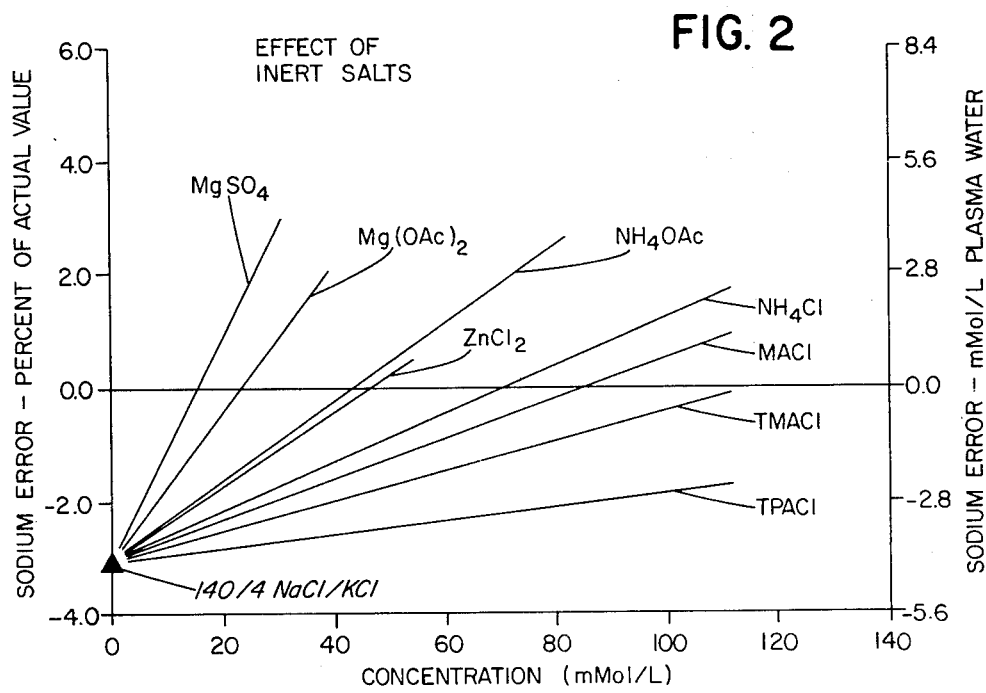

COMPENSATED REFERENCE LIQUID

This application is a continuation-in-part of U.S. Ser. No. 170,599 filed July 21, 1980, now abandoned.

This invention relates to chemical analyzers and more particularly to reference liquid systems for calibration or quality control of such analyzers of the ion-selective electrode type.

Development of ion-selective electrode (ISE) systems enables measurement of a wide variety of cations (positively-charged ions) and anions (negatively-charged ions); and particular ISE systems utilize sodium and potassium ion-selective electrodes for direct electrolyte analysis on undiluted samples (e.g., whole blood, plasma and serum) as well as indirect analysis on diluted samples (e.g., urine). Blood serum is a complex biological fluid containing various components of substantial physiological importance, and the determination of electrolytes, and particularly sodium and potassium is an important aspect of blood analysis. Published comparisons of data for sodium and potassium taken on ion-selective electrode analyzers with flame photometer data show essentially no bias for potassium but a moderate (3%) bias for sodium. However, for normal samples, electrolyte data expressed on a plasma water basis (direct measurement) should yield concentration data that varies from indirect procedure data by about seven percent. The plasma portion of a blood sample contains both electrolyte and non-electrolyte components, the non-electrolytes consisting primarily of dissolved and suspended proteins and lipids. The direct ISE mesurement is sensitive only to the electrolyte phase and yields concentrations on a plasma water basis, i.e., mMol/L plasma water, and provides valuable clinical information, especially for samples containing abnormal protein and or lipid levels. In addition, the need for centrifugation and dilution steps required for flame photometry and other indirect (diluted) methods is also eliminated. The indirect (diluted) flame photometry procedure utilizes an aliquot that contains both electrolyte and non-electrolyte phases and yields concentrations on a total plasma basis, mMol/L plasma. For this reason, all measurements incorporating a dilution step (including those made with ISE analyzers) have an inherent disadvantage in that they vary as some function of the lipid and protein concentrations.

Ion selective elecrode systems have unique characteristics which make them particularly advantageous for direct (undiluted) analysis, including response selectively to one type of ion so that, in general, interference from other ions in the test sample does not occur, and lack of response to dissolved and suspended solids such as blood cells, proteins, and lipids. An ion-selective electrode consists of an electrochemical half-cell (an internal electrolyte solution and an internal reference electrode) and a sensing membrane. The material of the sensing membrane depends on the particular ion to be measured; for example, a sodium electrode may have a glass capillary membrane similar to that in some flow-through pH electrodes, and a potassium electrode may have a polyvinyl chloride membrane that contains valinomycin. An ISE electrode measurement typically uses a reference electrochemical half-cell (for example, a silver/silver chloride electrode in contact with a concentrated potassium chloride solution) with an electrical connection between the reference electrode and the ion selective electrode by a salt bridge solution which may also be a concentrated solution of potassium chloride. In such systems, there is a small but significant voltage (termed a liquid junction potential $(E_j)$) at the boundary between the sample and salt bridge solutions that arises from the fact that ions of the two solutions diffuse at different rates across the boundary. The liquid junction potential will vary slightly depending on the composition of the sample or test solution and this can lead to error.

Electrolyte analysis systems designed for direct potentiometry in undiluted samples (whole blood, plasma and serum) and for indirect potentiometry in diluted samples (urine) use as a set of calibration solutions to calibrate the sodium and potassium electrodes: a first calibrant that has a dual function: midpoint calibration for the direct potentiometry mode and sloping calibration for the indirect potentiometry mode; a second calibrant that also has a dual function: sloping calibration for the direct potentiometry mode and midpoint calibration for the indirect potentiometry mode (and preferably has sodium and potassium ion concentrations similar to that of the diluted urine sample); and a urine diluent that preferably has sufficient pH buffering capacity to prevent the pH of diluted urine from falling below a pH of 5 and that stabilizes the ionic strength of the diluted urine so as to minimize errors due to variations in the urine ionic composition from sample to sample; and a set of linearity control solutions for routine checking of the analytical instrument. The sodium and potassium assay values for the midpoint calibrant and controls should be the same as the assay values for flame photometry measurements as historically, flame photometry has been the standard method for sodium and potassium assays. However, calibration fluids for flame photometry, which typically consist of sample mixtures of sodium chloride and potassium chloride, do not yield accurate calibration for direct measurements with ion-selective electrodes. These errors are due to sample matrix effects, primarily the activity coefficient and liquid junction potential factors. These errors can be overcome with a proper compensation system.

The potential of the ion selective measuring electrode $(E_{ISE})$ is logarithmically related to the activity of the ion of interest according to the Nernst equation. For the monovalent cation $M^+$, $$E_{ISE} = E^\circ_{ISE} + 2.303 \frac{RT}{F} \log a_{M^+} \tag{1}$$

where $E_{ISE}^\circ$ = standard potential (a constant) including terms due to the internal reference electrode, etc.

R = universal gas constant,

T = temperature in degrees Kelvin,

F = Faraday's constant, $a_{M^+}$ = activity of the ion $M^+$ being measured.

The quantity 2.303 (RT/F) is referred to as the slope (S) of the electrode and equals the number of volts the electrode output would change if the activity of $M^+$ were changed tenfold.

The symbol $a_{M^+}$ is referred to as the activity of the sample ion and it can be considered to be the "effective concentration" of the ion in the test solution. For clinical samples, this is always less than the millimolar concentration (mMol/L), where:

$$a_{M^+} = \gamma_{M^+} \cdot C_{M^+} \tag{2}$$

with:
$C_{M+}$ = concentration of the cation to be measured, and
$\gamma_{M+}$ = activity coefficient of the cation to be measured.

Substitution for $a_{M+}$ from Equation 2 into Equation 1 for monovalent ions (e.g., $Na^+$, $K^+$):

$$E_{ISE} = E_{ISE}° + (\text{Slope}) \log (C_{M+} \cdot \gamma_{M+}) \qquad (3)$$

$$E_{measured} = E_{ISE}° + (\text{Slope}) \log (C_{M+} \cdot \gamma_{M+}) - E_{REF} - E_j \qquad (4)$$

where
$E_{REF}$ = the potential of the reference electrode, and
$E_j$ = the liquid junction potential.

This equation can be written for both the sample (S) and the calibrant (C) solutions.

$$E_{meas}(S) = E_{ISE}° + (\text{Slope}) \log C_{M+}(S) \cdot \gamma_{M+}(S) - E_{REF} - E_j(S) \qquad (5A)$$

$$E_{meas}(C) = E_{ISE}° + (\text{Slope}) \log C_{M+}(C) \cdot \gamma_{M+}(C) - E_{REF} - E_{REF} - E_m(C) \qquad (5B)$$

The difference in measured potential, $\Delta E$ meas, between the sample and calibrant (i.e., Equations 5A–5B) is a measure of the concentration of $M^+$ in the sample. $E_{ISE}°$ and $E_{REF}$ are unchanged from sample to calibrant and, therefore, cancel.
Thus $$\Delta E_{meas.}(S) - (C) = (\text{Slope}) \log \left[ \frac{C_{M+}(S) \cdot \gamma_{M+}(S)}{C_{M+}(C) \cdot \gamma_{M+}(C)} \right] - \Delta E_j(S) - (C) \qquad (5)$$

where:
$\Delta E_j$ = residual liquid junction potential which equals the difference in the junction potential between sample and calibrant.

Taking the antilog and solving for the concentration of $M^+$ in the sample:

$$C_{M+}(S) = C_{M+}(C) \cdot \exp_{10}\left(\frac{\Delta E_{meas}(S) - (C)}{(\text{Slope})}\right) \cdot \left(\frac{\gamma_{M+}(C)}{\gamma_{M+}(S)}\right) \cdot \exp_{10}\left(\frac{\Delta E_j(S) - (C)}{(\text{Slope})}\right) \qquad (6)$$

This is the exact expression relating the concentration of the sample ion to the difference in the observed cell potential between the sample and calibrant. Similarly, the expression used to calculate the true slope of an ion-selective electrode can be written as:

$$\text{Slope} = \frac{\Delta E_{meas}(2) - (1) + \Delta E_j(2) - (1)}{\log \frac{C_{M+}(2)}{C_{M+}(1)} + \log \frac{\gamma_{M+}(2)}{\gamma_{M+}(1)}} \qquad (7)$$

Where the terms are as defined above and the numbers (1) and (2) refer to the midpoint and sloping calibrants respectively.

When using ISE analyzers for indirect potentiometry on highly diluted samples, the ionic strength and composition of both samples and calibrants is predominantly fixed by the diluent. As a result, the activity coefficients and junction potentials for all samples and the calibrants are essentially identical and equations 6 and 7 simplify to:

$$C_{M+(obs)}(S) = C_{M+}(C) \times \exp_{10}\left[\frac{\Delta E_{meas}(S) - (C)}{\text{Slope}}\right] \qquad (8)$$

and $$\text{Slope}_{(obs)} = \frac{\Delta E_{meas}(2) - (1)}{\log \frac{C_{M+}(2)}{C_{M+}(1)}} \qquad (9)$$

In practice when performing direct potentiometry on undiluted samples, it is convenient to use these simplified equations. This is because the values of the activity coefficient and junction potential terms are not generally known and cannot be determined readily for routine analysis. However, use of these simplified equations leads to errors in the assay value of the ions of interest according to:

$$\% \text{ Error in Reported Data} = \frac{C_{M+(obs)} - C_{M+(act)}}{C_{M+(act)}} \times 100 \qquad (10)$$

where $C_{M+(obs)}$ is the observed sample concentration as determined by the simplified equations (8) and (9), and $C_{M+(act)}$ is the actual concentration as determined by the exact equations (6) and (7). Substituting equation (6) through (9) into equation (10), the % Error can be written as:

$$\% \text{ Error} = \left[ \underbrace{\exp_{10}\left(\frac{-\Delta E(S)-(C)}{\text{Slope}_{(Actual)}}\right)}_{A} \times \underbrace{\exp_{10}\left(\frac{\Delta E(S)-(C)}{\text{Slope}_{(obs)}}\right)}_{B} \times \underbrace{\exp_{10}\left(\frac{-\Delta E_j(S)-(C)}{\text{Slope}_{(Actual)}}\right)}_{C} \times \underbrace{\frac{\gamma_{M+}(S)}{\gamma_{M+}(C)}}_{D} - 1 \right] \times 100 \qquad (11)$$

where $\text{Slope}_{(Actual)}$ corresponds to that obtained by equation (7) and $\text{Slope}_{(obs)}$ corresponds to the observed slope calculated with equation (7).

In equation 11, the terms A and B reflect the error introduced in the sample value as a result of using the simplified equation (6) rather than the exact equation (7).

This error arises from a mismatch of the activity coefficient and junction potential factors between the midpoint and slope calibrants. If the calibrants are well matched, $\text{Slope}_{(obs)}$ equals $\text{Slope}_{(Actual)}$ and terms A.B cancel. In addition equation 11 shows that slope errors have no effect on assay values for samples corresponding to the midpoint calibrant, that is, when $\Delta E_{meas}(2) - (1) = 0$.

Error term C in equation 11 results from the mismatch in the liquid junction potential between the sample and the calibrant. For example the use of a simple 140/4 mM solution of NaCl/KCl would yield a residual junction potential relative to normal blood, of 0.42 mV and this causes a low assay of about 1.6 percent. Error term D arises from differences in the activity coefficients between the ion of interest in the sample and calibrant. For example the activity coefficient for sodium ion in normal blood is 0.740 while the coefficient in a 140/4 NaCl/KCl calibrant is 0.751. This mismatch of $\gamma_{Na^+}$ would cause a low reading of the sodium value by 1.5 percent. Thus the total sodium error resulting from the use of a 140/4 NaCl/KCl calibrant would be about $-3.1$ percent.

Improved ISE analyzer reference liquids (e.g., calibrants and controls) in accordance with the invention contain compensation salts which adjust the values of activity coefficient and junction potential factors to reduce the error in the assay value, of the ion of interest at least fifty percent from that of an uncompensated liquid. The activity coefficient factor is:

$$\frac{\gamma_{M^+}(S)}{\gamma_{M^+}(C)} \qquad (12)$$

and the junction potential factor is:

$$\exp_{10}\left(\frac{-\Delta E_j(S) - (C)}{\text{slope}}\right) \qquad (13)$$

Accurate calibration for assay of biological fluids is obtained by the use of preferred compensated calibrants in which the C and D error terms in equation (11) have a product of essentially unity. In addition, the same compensation concept can be used to prepare control fluids which mimic biological samples over the physiological range and which can be used to test an analyzer for proper operation. In practice compensation is achieved with salts which adjust the junction potential factor, adjust the activity coefficient factor, or adjust both factors simultaneously. Depending on the particular case, these effects may be additive or subtractive. In sodium-potassium analyzer reference liquids, compensation may be obtained, for example, by subtituting other anions for chloride or by adding additional salts to a simple NaCl/KCl solution.

BRIEF DESCRIPTION OF DRAWINGS

FIG. 1 is a graph indicating error correction trends with alternate anions substituted after compensation salt; and FIG. 2 is a graph indicating the effect of addition of inert salts as compensation salts.

Error correction trends on a sodium ISE system (referenced to normal blood) with alternate anions substituted as the compensation salt for the chloride anion are indicated in FIG. 1. With a fixed cation composition and ionic strength (sodium and potassium levels held at 140/4 and monovalent anions substituted for chloride ion) the lower the equivalent conductance of the substituting anion the more positive is the shift in sample error as indicated in FIG. 1. This shift is due to changes in the activity coefficient and liquid junction potential. The use of divalent anions tends to cause steeper correction factor trends due to the increasing ionic strength which enhances the change in the activity coefficient.

The effect of addition of inert salts (i.e., those not containing the ion to be measured) as compensation salts to manipulate the activity coefficient and/or junction potential terms for a sodium electrode is indicated in FIG. 2. Over a limited concentration range, some salts such as magnesium sulfate and magnesium acetate tend to affect the activity coefficient more than the junction potential and in general multivalent salts have more of an effect than monovalent salts. Quaternary ammonium chloride salts alter both activity coefficient and junction potential. As indicated in FIG. 2, the slopes of the error lines for tripropylammonium chloride (TPACl) and tetramethylammonium chloride (TMACl) are lower than that of methylammonium chloride (MACl). Potassium ISE electrode systems have similar, but not identical, trends. Thus it is evident that a multitude of improved compensated reference liquid formulations exist.

Table 1 shows concentrations, and activity coefficient and junction potential values (calculated using the Debye-Hückel and Henderson equations) of ions in a typical adult blood sample (at 25° C.) on a plasma water basis with a 3 M KCl salt bridge and an open static junction.

TABLE 1

| Ion | Concentration (mMol/L) | Activity Coefficient |
|---|---|---|
| $Na^+$ | 150.0 | .740 |
| $K^+$ | 4.3 | .709 |
| $Ca^{++}$ | 2.7 | .344 |
| $Mg^{++}$ | 1.6 | .395 |
| $HCO_3^-$ | 29.0 | .740 |
| $H_2PO_4^-$ | .5 | .740 |
| $HPO_4^=$ | .8 | .285 |
| $Cl^-$ | 111.0 | .709 |
| $A^-$ (protein) | 21.5 | ~.617 |

Ionic strength (mMol/l): 168.0
Liquid junction potential is: 1.27 mV

In a particular embodiment, a system of calibrants, diluent and controls for an ion-selective electrode analyzer with sodium and potassium electrodes includes a first calibrant solution having the following composition:

TABLE 2

| Component | | Concentration |
|---|---|---|
| Formula | Name | (mMol/L) |
| NaCl | Sodium Chloride | 80.0 |
| NaOAc (anhydrous) | Sodium Acetate | 60.0 |
| KCl | Potassium Chloride | 4.00 |
| Mg(OAc)$_2$.4H$_2$O | Magnesium Acetate | 4.0 |
| CH$_2$O | Formaldehyde | 53 | a modified (and presently preferred) first calibrant solution having the following composition:

TABLE 3

| Component | | Concentration |
|---|---|---|
| Formula | Name | (mMol/L) |
| NaCl | Sodium Chloride | 63.0 |
| NaOAc (anhydrous) | Sodium Acetate | 77.0 |
| KCl | Potassium Chloride | 4.00 |
| Mg(OAc)$_2$.4H$_2$O | Magnesium Acetate | 4.0 |
| CH$_2$O | Formaldehyde | 53 | a second calibrant solution having the following composition:

TABLE 4

| Component | | Concentration |
|---|---|---|
| Formula | Name | (mMol/L) |
| NaCl | Sodium Chloride | 10.00 |
| KCl | Potassium Chloride | 7.00 |
| Mg(OAc)$_2$.4H$_2$O | Magnesium Acetate (tetrahydrate) | 50 |
| MgSO$_4$ (anhydrous) | Magnesium Sulfate | 13.0 |

TABLE 4-continued

| Component | | Concentration |
|---|---|---|
| Formula | Name | (mMol/L) |
| CH₂O | Formaldehyde | 53 | a urine diluent having the following composition:

TABLE 5

| Component | | Concentration |
|---|---|---|
| Formula | Name | (mMol/L) |
| Mg(OAc)₂·4H₂O | Magnesium Acetate (tetrahydrate) | 60.0 |
| MgSO₄ (anhydrous) | Magnesium Sulfate | 15.0 |
| CH₂O | Formaldehyde | 53 | a first linearity (120/2) control having the following composition:

TABLE 6

| Formula | Concentration (mMol/L) |
|---|---|
| NaCl | 55.0 |
| NaOAc | 65.0 |
| KCl | 2.00 |
| CH₂O | 53 | a second linearity (140/5) control having the following composition:

TABLE 7

| Formula | Concentration (mMol/L) |
|---|---|
| NaCl | 63.0 |
| NaOAc | 77.0 |
| KCl | 5.00 |
| Mg(OAc)₂·4H₂O | 4.00 |
| CH₂O | 53 | and a third linearity (160/8) control having the following composition:

TABLE 8

| Formula | Concentration (mMol/L) |
|---|---|
| NaCl | 63.0 |
| NaOAc | 97.0 |
| KCl | 8.00 |
| CH₂O | 53 |

The first calibrant solution (Table 2) has a sodium content of 140 mM; a potassium concentration of 4 mM; and an ionic strength of 156 mM. An uncompensated (140/4) calibrant solution ($E_j=0.85$, $\gamma_{Na}=0.751$, $\gamma_K=0.722$ and slope=58) has a calculated activity coefficient-junction potential sodium error of $-3.1$ percent and potassium error of $-3.4$ percent while the compensated calibrant (Table 2) ($E_j=1.28$, $\gamma_{Na}=0.746$, $\gamma_K=0.716$ and slope=58) has a sodium error of $-0.8$ percent and a potassium error of $-0.9$ percent. With this formulation, the mean bias between ion-selective electrode data (reduced to total plasma basis) and flame photometry data for ten normal blood samples from ambulatory donors was $0.1\pm0.3$ mMol/L (total plasma) for sodium and $0.11\pm0.06$ mMol/L (total plasma) for potassium.

A modified first calibrant solution (Table 3) also has a sodium content of 140 mM; a potassium concentration of 4 mM; and an ionic strength of 156 mM. The modified compensated (140/4) calibrant (Table 3) ($E_j=1.42$, $\gamma_{Na}=0.746$, $\gamma_K=0.716$, and slope=58) has a sodium error of $-0.2$ percent and a potassium error of $-0.4$ percent. With this formulation, the mean bias between ion-selective electrode data (reduced to total plasma basis) and flame photometry data for sixteen normal serum samples from hospitalized donors was $0.5\pm1.4$ mMol/L (total plasma) for sodium and $0.0\pm0.1$ mMol/L (total plasma) for potassium.

The second calibrant (Table 4) is used as the midpoint calibration for urine analysis and its sodium and potassium levels correspond to those of an average diluted urine sample on the basis of a dilution ratio of one part urine to six parts diluent, typical sodium levels being 70 mMol/L and typical potassium levels being 45 mMol/L. The 50 mMol/L magnesium acetate constituent adjusts the ionic strength of the second calibrant to be near that of the first calibrant and acts as an ionic strength and pH buffering agnet, and sample errors due to the activity coefficients and residual junction potentials errors are minimized by using the same salt in both the second calibrant and the diluent. Both magnesium acetate and magnesium sulfate compensation components tend to decrease the observed potassium slope and increase the observed sodium slope, the potassium electrode slope being more sensitive to these component concentrations than the sodium electrode slope for this calibration system.

The urine diluent (Table 5) has a background composition similar to that of the second calibrant (Table 4) and sufficient pH buffering capacity to maintain the pH of the diluted urine specimen above pH 5 (to avoid hydrogen ion interference at the sodium glass electrode); and sufficiently high ionic strength to minimize the influence of the urine sample on the final ionic strength and background of the diluted sample. Therefore, the magnesium acetate and magnesium sulfate compositions were chosen at a ratio of 7/6 times the concentrations in the second calibrant solution, so that the final ionic strength of the diluted sample is determined primarily by the diluent and the diluted sample closely resembles the second calibrant (Table 4).

Using the second calibrant and diluent compositions, ion-selective electrode and flame photometry assay values were compared for 36 urine samples with excellent correlation over the physiological ranges for both sodium and potassium.

Both sodium/potassium ISE analyzers and flame photometers have approximately the same operational range of sodium and potassium concentrations, the sodium range (physiologically) being 115 to 190 mM and the potassium range being 1.5 to 9 mM. Such analytical instruments are routinely tested using well characterized controls near and away from the midpoint. The three linearity controls (Tables 6-8) are compatible with both ISE analyzers and flame photometers. Preferably, these controls are colored for easy identification and diagnostic purposes. Linearity control solutions of pure NaCl and KCl assayed on an ISE analyzer calibrated for accurate assay of blood sample yield numbers which are high by about 3-4 percent, due to mismatch between liquid junction potentials and activity coefficients. Error reduction in the compensated linearity controls (Tables 6-8) is summarized in Table 9.

TABLE 9

|  | % Sodium Error | | % Potassium Error | |
|---|---|---|---|---|
|  | Uncompensated | Compensated | Uncompensated | Compensated |
| 120/2 (Table 6) | 3.3 | 1.0 | 3.5 | 1.2 |
| 140/5 (Table 7) | 3.0 | −0.1 | 3.1 | −0.1 |
| 160/8 (Table 8) | 2.7 | −0.2 | 2.9 | 0.0 |

These values were calculated from error terms C and D in equation (11) with the subscript (S) referring to the linearity control solution and (C) referring to a blood sample with the same levels of sodium and potassium as the control and normal levels of other constituents and with calculated activity coefficient and junction potential values on the same basis as in Table 1 as follows:

TABLE 10

|  |  | $E_j$ | $\gamma_{Na}$ | $\gamma_K$ |
|---|---|---|---|---|
| 120/2 | Reference Blood (C) | 1.52 | .755 | .727 |
|  | Uncompensated (S) | .97 | .763 | .736 |
|  | Compensated (S) | 1.53 | .763 | .736 |
| 140/5 | Reference Blood (C) | 1.35 | .744 | .714 |
|  | Uncompensated (S) | .85 | .751 | .722 |
|  | Compensated (S) | 1.41 | .745 | .715 |
| 160/8 | Reference Blood (C) | 1.20 | .735 | .702 |
|  | Uncompensated (S) | .73 | .741 | .709 |
|  | Compensated (S) | 1.45 | .741 | .709 |

In these particular controls, the $Cl^-/OAc^-$ ratio is altered so as to produce the equivalent assay results both on ISE analyzers properly calibrated for blood and on flame photometers.

Various combinations of blue, red, and yellow dyes were used to produce the following colors:

| 140/4 | (Table 3) | blue |
|---|---|---|
| 10/7 | (Table 4) | red |
| 120/2 | (Table 6) | purple |
| 140/5 | (Table 7) | green |
| 160/8 | (Table 8) | orange |

The 140/4, 10/7, 140/5 and 120/2 solutions each have about 100 parts per million of dye added (100 mg/L). The same intensity was achieved for the 160/8 solution with 200 mg/L of dyes. The dyes were assayed for sodium content in order to properly adjust the NaCl in the formulation (Table 11).

TABLE 11

$Na^+$ CONTENT OF DYES

| Dye | Increase in $Na^+$ (mM) Per 100 mg Dye |
|---|---|
| Pyla-Cert Red #33 | 0.50 |
| W.J. #5601 Blue #1 | 0.25 |
| W.J. #8005 Yellow #5 | 0.45 |

Formulations for colored calibrants and linearity controls are summarized in Table 12:

TABLE 12

|  | Calibrants | | Linearity Controls | | |
|---|---|---|---|---|---|
|  | 140/4 | 10/7 | 120/2 | 140/5 | 160/8 |
| NaCl | 62.75 | 9.60 | 54.61 | 62.58 | 62.02 |
| NaOAc | 77.00 | — | 65.00 | 77.00 | 97.00 |
| KCl | 4.00 | 7.00 | 2.00 | 5.00 | 8.00 |
| $Mg(OAc)_2 \cdot 4H_2O$ | 4.00 | 50.00 | — | 4.00 | — |
| $MgSO_4$ anhydrous | — | 13.00 | — | — | — |
| $CH_2O$ | 53 | 53 | 53 | 53 | 53 |
| Red #33 | — | 100 mg/L | 70 mg/L | — | 40 mg/L |
| Blue #1 | 100 mg/L | — | 30 mg/L | 40 mg/L | — |
| Yellow #5 | — | — | — | 60 mg/L | 160 mg/L |

The salts in these reference solutions are stable, commonly available reagents that do not interfere with the response of either electrode. The formaldehyde preservative prevents any appreciable bacterial or mold growth in the reagents without requiring sterilization and does not damage or interfere with either the sodium or potassium ion-selective electrodes.

These reference liquid formultations reduce activity coefficient and liquid junction potential error effects and provide assay values on normal blood samples (reduced to total plasma basis) for sodium and potassium that are the same as determined by flame photometry and other analyzers using indirect (diluted) methods.

While these reference liquid systems are particularly advantageous in biological fluid analysis systems of the ISE types, it will be apparent that other reference liquid systems in accordance with the invention may be developed for other ions and for other applications such as on-line monitoring and direct process control. Therefore, while particular embodiments of the invention have been shown and described, various modifications will be apparent to those skilled in the art and therefore it is not intended that the invention be limited to the disclosed embodiments or to details thereof and departures may be made therefrom within the spirit and scope of the invention.

What is claimed is:

1. A compensated reference liquid for use with a chemical analyzer that has an ion selective electrode comprising
   a first component that provides ions of a first element to be measured present in a predetermined concentration, and an error compensation component for adjusting
   (a) the activity coefficient factor (Equation 12), and-/or
   (b) the junction potential factor (Equation 13)
   said error compensation component being present in a concentration sufficient to reduce the error in said compensated reference liquid at least fifty percent from the error in a corresponding reference liquid without said error compensation component.

2. A reference liquid as claimed in claim 1 for use with a chemical analyzer that has a plurality of ion selective electrodes for direct potentiometry of undiluted specimens, said reference liquid further including a second component that provides ions of a second element to be measured in a predetermined concentration.

3. The reference liquid of claim 2 wherein said first element is sodium and said second element is potassium.

4. The reference liquid of any preceding claim and further including a preservative in said liquid.

5. The reference liquid of any of claims 1-3 wherein said error compensation component is a water soluble salt.

6. The liquid of claim 5 wherein said water soluble salt is an added inert salt.

7. The reference liquid of claim 5 wherein said water soluble salt is a compensation salt of the alternate anion type.

8. The reference liquid of any of claims 1-3 wherein the product of said activity coefficient factor and said junction potential factor essentially is unity.

9. The reference liquid of any of claims 1-3 wherein the concentration of ions of said first element in said reference liquid is such that analysis of said reference liquid with a chemical analyzer of the flame photometer type provides correlated results.

10. A reference liquid system for a chemical analyzer that has a plurality of ion selective electrodes for direct potentiometry of undiluted specimens comprising a plurality of reference liquids, each as claimed in claim 1, each said reference liquid including salts in predetermined concentration of first and second elements to be measured, a first of said reference liquids being a first calibrant that comprises salts of said first and second elements in predetermined concentration for providing midrange calibration for undiluted specimens and slope calibration for diluted specimens, and a second of said reference liquids being a second calibrant that contains salts of said first and second elements in a concentration different from the concentration of said salts in said first calibrant, said second calibrant providing midrange calibration for diluted specimens and slope calibration for undiluted specimens.

11. The reference liquid system of claim 10 and further including a diluent comprising an error compensation component of said second calibrat present in a concentration sufficient to maintain a diluted specimen at pH higher than 5, and having an ionic strength of at least 150 mMol/L.

12. A reference liquid system for a chemical analyzer that has a plurality of ion selective electrodes for direct potentiometry of undiluted specimens comprising a plurality of reference liquids, each as claimed in claim 1, each said reference liquid including salts in predetermined concentration of first and second elements to be measured, a first of said reference liquids being a midpoint control, a second of said reference liquids being a control offset from said midpoint control, and a third of said reference liquids being a control offset in the other direction from said midpoint control.

13. The reference liquid system of any of claims 10-12 wherein each said reference liquid contains dye material to distinctively color said reference liquid, the concentrations of ions of said first element in each said reference liquid being adjusted to compensate for ions of said first element in the dye material in that reference liquid.

14. The reference liquid system of claim 13 wherein said first element is sodium and said second element is potassium.

15. The reference liquid system of claim 14 and further including a preservative in each said liquid.

16. The reference liquid system of claim 15 wherein each said error compensation component is a water soluble salt.

17. The reference liquid system of claim 16 wherein the product of said activity coefficient factor and said junction potential factor in at least one of said reference liquids essentially is unity.

18. A calibrant solution for the calibration of a chemical analyzer that has sodium and potassium ion selective electrodes comprising:

a first component that has a predetermined concentration of sodium ions, a second component that has a predetermined concentration of potassium ions, and an error compensation component present in a concentration such that the product of:

(a) the ratio of the activity coefficients of the sodium and potassium ions in said calibrant solution and in an undiluted speciment to be analyzed and (b) the logarithmic quantity ($\exp_{10}$) of the difference between the liquid junction potentials of said calibrant solution and said undiluted specimen to be analyzed divided by the slope of the ion selective electrode essentially is unity.

19. A calibrant system for the calibration of a chemical analyzer that has a plurality of ion selective electrodes for direct potentiometry of undiluted specimens comprising a first calibrant comprising a first component that has a predetermined concentration of sodium ions, a second component that has a predetermined concentration of potassium ions, and an error compensation component present in a concentration such that the product of:

(a) the ratio of the activity coefficients of the sodium and potassium ions in said first calibrant and an undiluted specimen to be analyzed and (b) the logarithmic quantity ($\exp_{10}$) of the difference between the liquid junction potentials of said first calibrant and the undiluted specimen to be analyzed divided by the slope of the ion selective electrode system essentially is unity;

a second calibrant comprising sodium and potassium salts present in a relative concentration different from the ion concentration of said first calibrant, and an error compensation component present in a concentration such that the product of:

(a) the ratio of the activity coefficients of the sodium and potassium ions of said second calibrant and said first calibrant and (b) the logarithmic quantity ($\exp_{10}$) of the difference between the liquid junction potentials of said first and second calibrants divided by the slope of the ion selective electrode system essentially is unity.

20. The system of claim 19 and further including a diluent comprising an error compensation component of said second calibrant present in concentration sufficient to maintain the diluted specimen at pH higher than 5, and having an ionic strength of at least 150 mMol/L.

21. The system of claim 19 wherein said first calibrant provides mid range calibration for undiluted specimens and slope calibration for diluted specimens and said second calibrant provides mid range calibration for diluted specimens and slope calibration for undiluted specimens.

22. The system of claim 19 wherein sodium ions are present in said first calibrant in a concentration of about 140 mMol/L, potassium ions are present in said first calibrant in a concentration of about 4 mMol/L, and the sodium/potassium ion concentration ratio in said second calibrant is about 10:7.

23. The system of claim 19 and further including a preservative in each said calibrant.

24. The system of either claim 18 or 19 wherein each said error compensation component is a water soluble salt.

* * * * *